(12) United States Patent
Reinke

(10) Patent No.: US 8,589,178 B2
(45) Date of Patent: Nov. 19, 2013

(54) EXTENSIBLE THERAPY DELIVERY SYSTEM AND METHOD THEREOF

(75) Inventor: Robert E. Reinke, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 658 days.

(21) Appl. No.: 12/207,975

(22) Filed: Sep. 10, 2008

(65) Prior Publication Data

US 2010/0063844 A1    Mar. 11, 2010

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC .......................................................... 705/2, 3
See application file for complete search history.

(56) References Cited

U.S. PATENT DOCUMENTS

| | | | |
|---|---|---|---|
| 4,731,726 A | 3/1988 | Allen, III | |
| 4,839,822 A | 6/1989 | Dormond et al. | |
| 4,924,408 A | 5/1990 | Highland | |
| 4,949,278 A | 8/1990 | Davies et al. | |
| 5,251,126 A | 10/1993 | Kahn et al. | |
| 5,283,856 A | 2/1994 | Gross et al. | |
| 5,404,292 A | 4/1995 | Hendrickson | |
| 5,442,792 A | 8/1995 | Chun | |
| 5,644,770 A | 7/1997 | Burke et al. | |
| 6,024,699 A | 2/2000 | Surwit et al. | |
| 6,081,786 A | 6/2000 | Barry et al. | |
| 6,277,071 B1 | 8/2001 | Hennessy et al. | |
| 6,641,532 B2 | 11/2003 | Iliff | |
| 7,260,480 B1 * | 8/2007 | Brown et al. | 702/19 |
| 7,320,030 B2 | 1/2008 | Brown | |
| 7,685,262 B2 * | 3/2010 | Choubey et al. | 709/220 |
| 8,000,977 B2 * | 8/2011 | Achan | 705/2 |
| 2004/0073464 A1 | 4/2004 | Huang | |
| 2004/0172284 A1 | 9/2004 | Sullivan et al. | |
| 2004/0249420 A1 * | 12/2004 | Olson et al. | 607/9 |
| 2007/0100659 A1 * | 5/2007 | Preiss | 705/2 |
| 2007/0276197 A1 | 11/2007 | Harmon | |

FOREIGN PATENT DOCUMENTS

| | | |
|---|---|---|
| EP | 1559364 A1 | 8/2005 |
| EP | 1722310 A1 | 11/2006 |
| EP | 1850226 A1 | 10/2007 |
| EP | 1593338 B1 | 1/2008 |

(Continued)

OTHER PUBLICATIONS

GlucoCom Telemonitoring for Diabetes Disease Management, http://www.glucocom.com/.
Aaron E. Carroll, et al., The HealthPia GlucoPak Diabetes Phone: A Usability Study, Diabetes Technology & Therapeutics, vol. 9, Nov. 2, 2007, pp. 158-164.

(Continued)

*Primary Examiner* — Neha Patel
(74) *Attorney, Agent, or Firm* — Dinsmore & Shohl LLP

(57) ABSTRACT

An extensible therapy delivery system for an individual having a clinical rules module providing an existing clinical rule and is extensible to receive a new validated clinical rule and method thereof are disclosed. The extensible system also provides a domain module having existing clinical data and base logic and is extensible to receive new clinical data and additional logic to support the new validated clinical rules. The extensible system also provides a data request interface that directs a request for information from the clinical rules for the determination of therapy for the individual to the domain module, which answers the request with the existing and new clinical data and logic. The extensible system delivers to the individual the therapy determined by the clinical rules module from using the answer to the request provided by the domain module.

16 Claims, 6 Drawing Sheets

(56) References Cited

FOREIGN PATENT DOCUMENTS

| WO | 02/21336 A2 | 3/2002 |
|---|---|---|
| WO | 2004/090503 A2 | 10/2004 |
| WO | 2006 002415 A1 | 1/2006 |
| WO | 2006/108304 A1 | 10/2006 |
| WO | 2006/108858 A1 | 10/2006 |
| WO | 2009/002415 A1 | 12/2008 |

OTHER PUBLICATIONS

M. Li, et al., 3G Network Oriented Mobile Agents for Intelligent Diabetes Management: A Conceptual Model, 0-7803-7667—Jun. 2003 IEEE, pp. I 31-I 34.

S.G. Mougiakakou, et al., A Communication Platform for Tele-monitoring and Tele-management of Type 1 Diabetes, Proceedings of the 2005 IEEE, Engineering in Medicine and Biology 27th Annual Conference, Shaghai, China, Sep. 1-4, 2005, pp. 2207-2210.

* cited by examiner

EXTENSIBLE THERAPY DELIVERY SYSTEM AND METHOD THEREOF

FIELD OF THE INVENTION

The present invention relates generally to chronic disease management, and more particularly, to an extensible therapy delivery system having a clinical rules module that is extensible to receive new validated clinical rules and a domain module extensible to receive new individual-specific clinical data and additional logic to determine therapy for an individual suffering from a chronic disease. Thereby, the extensible therapy delivery system used by the individual need not be replaced in order to implement into a therapy regimen new medical advances involved in determining therapies for treatment of chronic conditions. The present invention further related to methods involving embodiments of extensible therapy delivery systems of the present invention.

BACKGROUND OF THE INVENTION

Prior art therapy delivery systems typically employ a hard-coded algorithm or hard-coded rules. As such, if a new rule, logic, algorithm, or calculation method for determining a medication, a therapy, or other, becomes available, existing deployed systems must be reconfigured with new algorithms or rules to test the new rule. Once the new rule is tested and validated as safe and effective in treating a chronic condition, the existing deployed systems must be wholly, or at least partially, replaced with a new system configured to support the new rule. Such replacements typically require patients and health care providers to learn the new system and expend significant amounts of money to acquire the new systems, rendering the managing of a chronic disease, such as diabetes, all the more difficult, time-consuming, and expensive.

SUMMARY OF THE INVENTION

It is against the above background that the present invention provides an extensible therapy delivery system having a clinical rules module that is extensible to receive new validated clinical rules and a domain module extensible to receive new individual-specific clinical data and additional logic to support the new validated clinical rules in determining therapy for an individual and related methods thereof. In other embodiments, the extensible therapy delivery system comprises a development environment and a deployed environment, wherein new clinical rules are drafted, edited, and validated in the development environment and deployed to a clinical rules module integrated into, for example, a mobile deployed application with the individual in the deployed environment.

In accordance with one embodiment of the present invention, an extensible therapy delivery system for an individual comprises a clinical rules module comprising one or more existing clinical rules and is extensible to receive one or more new validated clinical rules. In addition, the extensible system further comprises a domain module comprising existing individual-specific clinical data and base logic and is extensible to receive new individual-specific clinical data and additional logic to support the new validated clinical rules. The extensible therapy delivery system further comprises a data request interface operably connected to the clinical rules module and the domain module, wherein the clinical rules module is programmed to make a request for information to the data request interface according to the existing clinical rules and the new validated clinical rules when provided in order to determine therapy for the individual, and the data request module is programmed to forward the request to the domain module which is programmed to answer the request using the new individual-specific clinical data and additional logic when provided if the existing individual-specific clinical data and base logic is unable to answer the request and, wherein the extensible system is configured to deliver to the individual the therapy determined by the clinical rules module from using the answer to the request provided by the domain module.

In accordance with another embodiment of the present invention, a method of determining therapy for an individual comprises: providing a therapy delivery system comprising an extensible clinical rules module, an extensible domain module, and a data request interface; extending the clinical rules module to integrate one or more new validated clinical rules with one or more existing clinical rules, the new validated clinical rules and the existing clinical rules being defined to determine therapy for the individual; extending the domain module to integrate new individual-specific clinical data and additional logic with existing individual-specific clinical data and base logic, the new individual-specific clinical data and additional logic being provided to support the new validated clinical rules of the clinical rules module for therapy determination for the individual; requesting information for therapy determination with the new validated clinical rules of the clinical rules module through the data request interface to the domain module; providing the requested information to the data request interface with at least one of the existing individual-specific clinical data and base logic and the new individual-specific clinical data and additional logic of the domain module; and determining therapy for the individual with the new validated clinical rules of the clinical rules module and the requested information provided from the domain module.

In accordance with another embodiment of the present invention, a method of integrating one or more new validated clinical rules in a deployed application of an existing therapy delivery system comprises: defining one or more new clinical rules for determining a therapy for an individual; validating the new clinical rules by testing the new clinical rules in a simulation module simulating one or more physiological conditions of the individual; editing and re-validating the new clinical rules as necessary to substantially eliminate any detrimental outcomes to health of the individual identified in the simulation module; deploying the new validated clinical rules with new individual-specific clinical data and additional logic to support the new validated clinical rules to the deployed application of the extensible system; extending a clinical rules module of the therapy delivery system to integrate the new validated clinical rules; extending a domain module of the therapy delivery system to integrate the new individual-specific clinical data and additional logic; and delivering the therapy to the individual with the therapy delivery system, the therapy determined by the new validated clinical rules.

BRIEF DESCRIPTION OF THE DRAWINGS

The following detailed description of the various embodiments of the present invention can be best understood when read in conjunction with the following drawings, where like structure is indicated with like reference numerals and in which.

Figure 1:
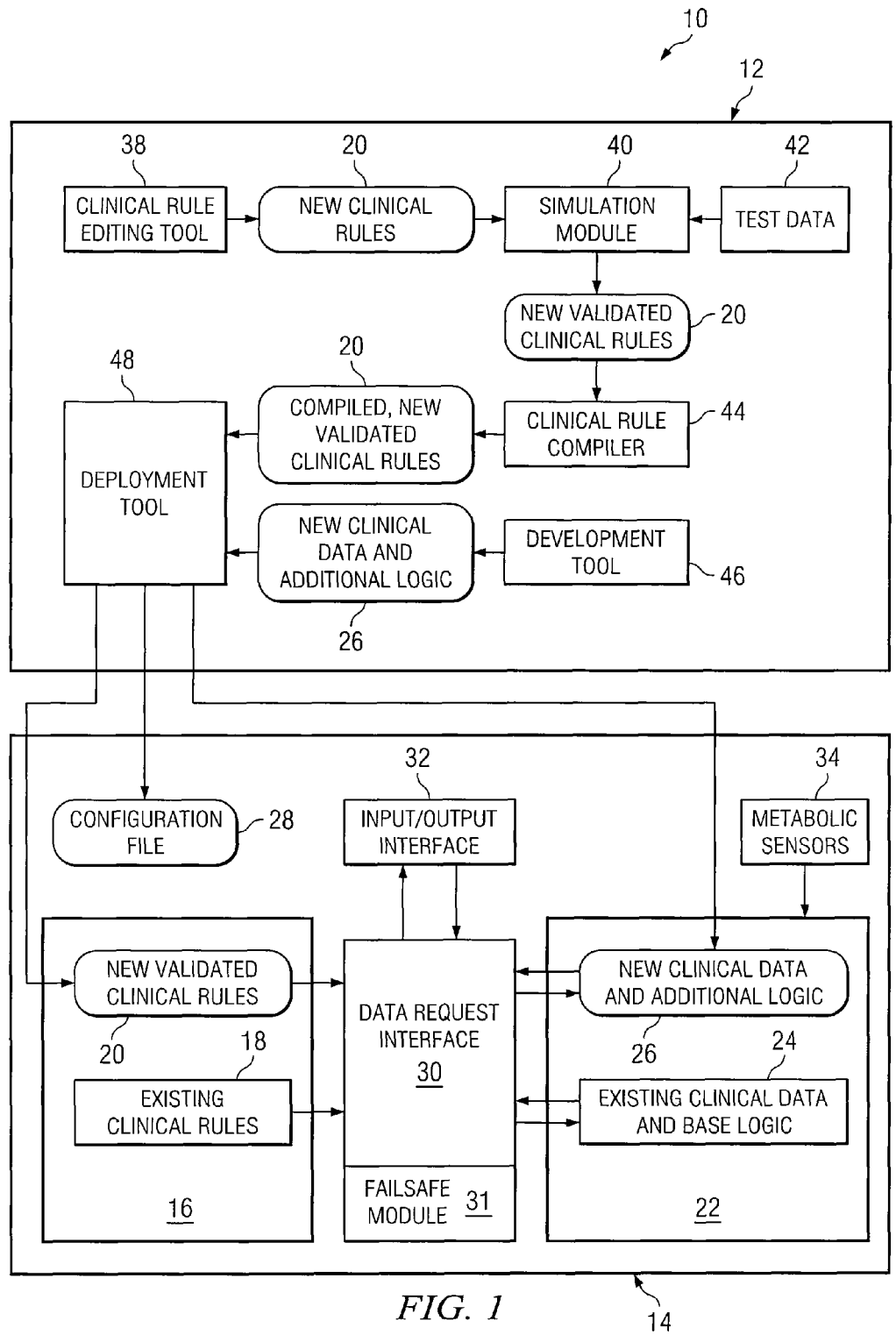
FIG. 1 is a block diagram of an extensible therapy delivery system according to one embodiment of the present invention.

The embodiments set forth in the drawings are illustrative in nature and are not intended to be limiting of the invention defined by the claims. Moreover, individual aspects of the drawings and the invention will be more fully apparent and understood in view of the detailed description.

DETAILED DESCRIPTION

Figure 2:
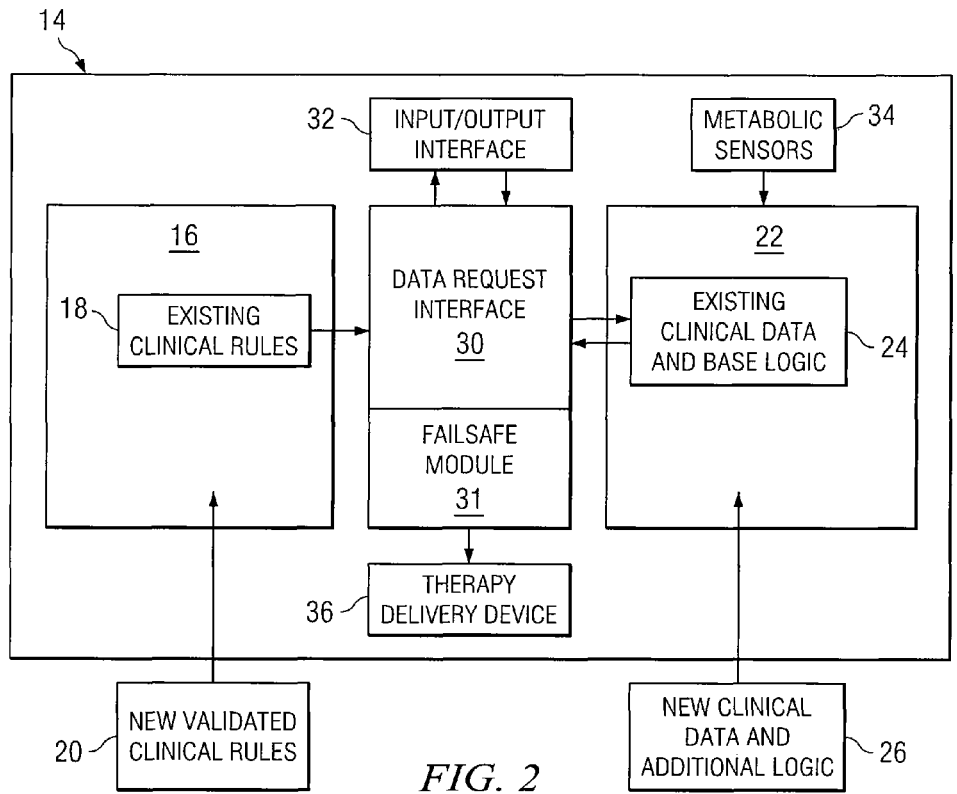
FIG. 2 is a block diagram of a deployed environment of an extensible therapy delivery system prior to integration of new validated clinical rules and new clinical data and additional logic therein according to another embodiment of the present invention.
Figure 3:
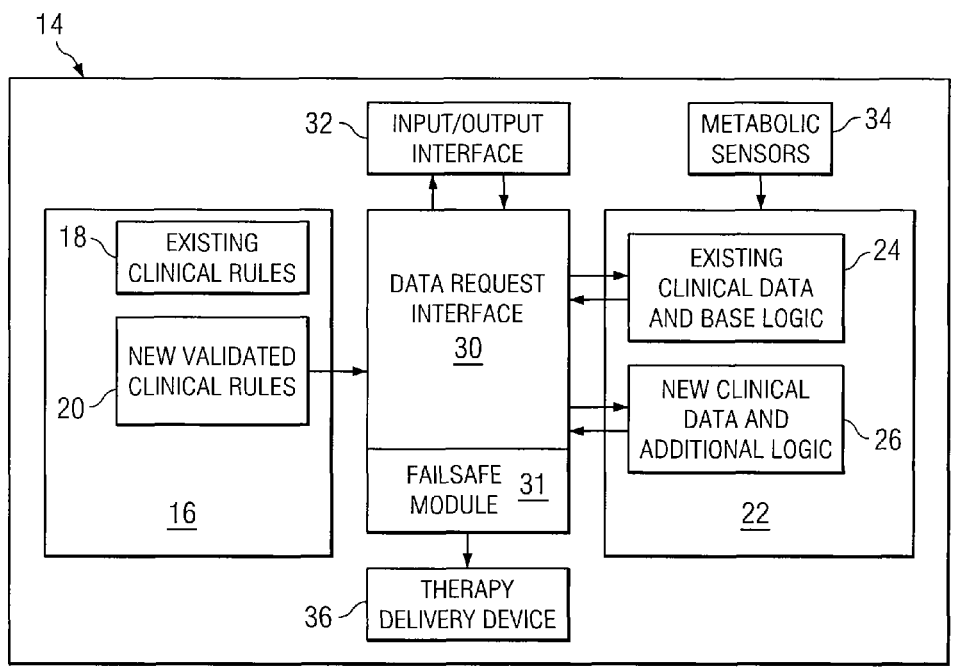
FIG. 3 is a block diagram of the deployed environment of the extensible therapy delivery system according to the embodiment of the present invention illustrated in FIG. 2 following integration of new validated clinical rules and new clinical data and additional logic therein.

Referring initially to FIGS. 1-3, an extensible therapy delivery (and/or guidance) system 10 (herein also referred to as "extensible system") for an individual generally comprises a clinical rules module 16, a domain module 22, and a data request interface 30. The clinical rules module 16 comprises one or more existing clinical rules 18 and is extensible to receive one or more new validated clinical rules 20. The clinical rules, whether those existing 18 or new 20, are used by the extensible system 10 to determine therapy for the individual. More particularly, the clinical rules 18, 20 may be algorithms uniquely defined and customized to therapeutic needs of the individual and evolving standards in the chronic disease management industry. Further, it is generally presumed that the existing clinical rules 18 have been validated through a testing or simulation mechanism or module, similar to or the same as that described herein with respect to the validation of the new clinical rules 20 or otherwise, prior to their employed in the extensible system 10 to determine therapy for an individual. For exemplary purposes only, in one embodiment, the therapy delivered to the individual by the extensible system 10 is insulin in a dosage amount, concentration, delivery rate, and/or delivery schedule determined by the existing clinical rules 18 and the new validated clinical rules 20. It is contemplated, however, that the therapy determined and delivered by an extensible system 10 may be any therapeutic aid provided to an individual to treat a chronic disease or condition.

The domain module 22 of the extensible system 10 comprises existing individual-specific clinical data and base logic 24 and is extensible to receive new individual-specific clinical data and additional logic 26. The existing and new individual-specific clinical data generally include information such as, but not limited to, physiological conditions, meals, exercise routines, archived clinical data, etc., specific to the individual utilizing the extensible system 10. Meanwhile, the base logic and the additional logic generally are code, software, or other similar technologies, that support an operation of the extensible system 10 and components thereof. The new individual-specific clinical data and additional logic 26 are often received by the domain module 22 simultaneously with the receipt of the new validated clinical rules 20 by the clinical rules module 16. Thereby, if necessary, the new individual-specific clinical data and additional logic 26 may support the new validated clinical rules 20 for therapy determinations for the individual. Generally, the new validated clinical rules 20 are supported by both the existing and the new clinical data and base and additional logic and may rely on the data and logic of either 24, 26, depending on which can answer the request for information sought by the new validated clinical rules 20 in determining therapy for the individual.

Further, it is contemplated that existing and new clinical data of the domain module 22 need not necessarily be specific to the individual using the extensible system 10. Rather, the existing and/or new clinical data may be general population clinical data alone or in combination with individual-specific clinical data. As such, existing individual-specific clinical data and new individual-specific clinical data are also referred to herein, and in the Figures, as existing clinical data and new clinical data, respectively. It is further contemplated that new clinical data and additional logic need not necessarily be received by the domain module 22 simultaneously. Rather, the domain module 22 may receive just new clinical data or just additional logic.

The data request interface 30 is operably connected to the clinical rules module 16 and the domain module 22. The clinical rules module 16 is programmed to make a request for information to the data request interface 30 according to the existing clinical rules 18 and the new validated clinical rules 20, when provided, in order to determine therapy for the individual. The data request interface 30 is programmed to forward the request for information to the domain module 22. The domain module 22 is programmed to answer the request for information using the new individual-specific clinical data and additional logic 26, when provided, if the existing individual-specific clinical data and base logic 24 is unable to answer the request.

Further, the data request interface 30 may comprise a failsafe module 31. The failsafe module 31 may defines one or more therapy limitations independent of the existing clinical rules 18 and the new validated clinical rules 20 for substantially preventing delivery of therapy outside of the therapy limitations. These therapy limitations may be specific to the individual and define the limitations of permissible therapy that may be delivered while avoiding substantial harm to the individual. Thereby, the failsafe module 31 safeguards against the delivery of therapy in amounts, concentrations, rates, etc. that may result in detrimental outcomes in the health of the individual. Thus, after the clinical rules 18, 20 determine a therapy from using the answer to the request provided by the domain module 22, the data request interface 30 may compare the determined therapy with the therapy limitations defined by the failsafe module 31. If the determined therapy complies with the therapy limitations, then the failsafe module 31 may direct the delivery of the therapy to the individual. However, if the determined therapy falls outside of the therapy limitations, then the failsafe module 31 may prevent the delivery of the determined therapy to the individual. Should the failsafe module 31 prevent the delivery of a therapy determined by the existing clinical rules 18 or the new validated clinical rules 20, the failsafe module 31 may transmit a signal to the input/output interface 32 to notify the individual of the prevention of the therapy delivery and of the possible need for the individual to contact a physician and/or direct the delivery of another therapy.

In one embodiment, the data request interface 30 also is extensible. More particularly, the data request interface 30 generally comprises an existing messaging framework and is extensible to receive one or more new messaging frameworks to support requests for information made by the new validated clinical rules 20 in determining therapy for the individual. Generally, the existing messaging framework and the new messaging frameworks of the data request interface 30 are employed in a message-based software architecture of the data request interface 30. It is also contemplated, however, that the data request interface 30 can be defined in hardware, rather than software, means or terms.

The extensibility of the clinical rules module 16, the domain module 22, and/or the data request interface 30 to receive the new validated clinical rules 20, the new individual-specific clinical data and additional logic 26, and the new messaging frameworks, respectively, do not interfere with an operational functionality of the hardware or software of the extensible system 10. Thereby, the extensible system 10 is configured to deliver to the individual the therapy determined by one of the existing clinical rules 18 and new validated clinical rules 20 of the clinical rules module 16 from using the answer to the request for information provided by one of the existing individual-specific clinical data and base logic 24 and new individual-specific clinical data and additional logic 26. As such, the extensible system 10 generally is configured to determine and deliver therapy to the individual both prior to and after the integration of the new validated clinical rules 20 into the clinical rules module 16 and/or the integration of the new individual-specific clinical data and additional logic 26 into the domain module 22. Thus, when it is medically necessary, recommended, or desired to determined therapy with a new or different clinical rule, such rules may be integrated into the extensible system 10 without having to replace entirely, or even partially, the extensible system 10, or a deployed application thereof, resulting in significant savings in time and money.

As further illustrated in FIG. 1, the extensible system 10 generally further comprises a development environment 12 and a deployed environment 14 operatively connected by a network connection such that data, such as, but not limited to, clinical rules, clinical data, logic, and any other therapy-related data, may be transmitted therebetween. The network connection may be provided via a wired or wireless internet or intranet connection. It is contemplated that the network connection may be secured by password or other means and the data transmitted thereover may be encrypted for security and/or privacy purposes.

The components of the extensible system 10 employed in the deployed environment 14 may be integrated into one or more deployed applications, which may be mobile, wireless applications. For example, in one embodiment, at least one of the mobile deployed applications is a personal digital assistant or a cellular phone and at least one other of the mobile deployed applications is a therapy delivery pump. The components of the extensible system 10 employed in the development environment 12, meanwhile, may be integrated into a computer system operatively connected by the network connection to the deployed applications in the deployed environment 14. It is contemplated that while the development environment 12 and the deployed environment 14 may be in the same computational environment, they generally are removed from one another and operate in separate environments operatively connected for the exchange of rules, data, and logic.

The clinical rules module 16, the domain module 22, and the data request interface 30 generally are employed in the deployed environment 14 with the individual. Whereas, one or more of the following components of the extensible system 10 generally are employed in the development environment 12: a clinical rule editing tool 38, a simulation module 40, a clinical rule compiler 44, a development tool 46, and a deployment tool 48. The components of the extensible system 10 employed in the development environment 12 generally are configured to create, edit, and validate new clinical rules 20 and to create new clinical data and additional logic 26 that may be deployed and integrated into the clinical rules module 16 and the domain module 22, respectively, in the deployed environment 14 to determine therapy for the individual.

The clinical rule editing tool 38 generally is configured to permit drafting and editing of new clinical rules 20 prior to integration into the clinical rules module 16. Generally, health care professionals, such as physicians or clinical experts, and engineers may cooperate in using the clinical rule editing too 38 to define one or more new clinical rules 20 to be integrated into the clinical rules module 16 to determine therapy in accordance with what typically is a newly discovered medically-favorable clinical rule for determining therapy. The clinical rule editing tool 38 generally supports abstractly and expressively defined clinical rules 20 and captures them in a format executable by a simulation module 40.

The simulation module 40 may be configured to validate new clinical rules 20 prior to integration into the clinical rules module 16. The simulation module 40 may perform this validation of the new clinical rules 20 by simulating with test data 42 of one or more physiological conditions of the individual and identifying detrimental health outcomes to the simulated physiological conditions of the individual caused by a simulated delivery of therapy determined by the new clinical rules 20. The test data 42 may also, or alternatively, include information pertaining to other individual-specific therapy-related data and/or data pertaining to physiological conditions or therapy-related data derived from selected populations. If any detrimental health outcomes are identified in the simulation module 40, then the new clinical rules 20 may be returned to the clinical rule editing tool 38 for editing to substantially eliminate the identified detrimental health outcomes. The edited new clinical rules 20 may then be re-submitted to the simulation module 40 for further testing. This process of editing and testing the new clinical rules 20 may be repeated as many times as necessary to validate the new clinical rules 20 as appropriate (i.e., no identified detrimental health outcomes) for integration into the clinical rules module 16.

In one embodiment, the clinical rule editing tool 38 is text editor, such as, but not limited to, the notepad tool in the Microsoft® operating system and the simulation module 40 is a customized software configured to interpret the text file produced by the clinical rule editing tool 38. In another embodiment, however, the clinical rule editing tool 38 and the simulation module 40 are incorporated into a common tool, such as, but not limited to, the Vanguard Studio™ produced by Vanguard Software Corporation.

Once validated by the simulation module 40, the new validated clinical rules 20 are transmitted to the clinical rule compiler 44. The clinical rule compiler 44 may be configured to convert the new validated clinical rules 20 into a form executable by the clinical rules module 16 to determine therapy for the individual prior to integration into the clinical rules module 16. More particularly, the rule compiler generally first converts the new clinical rules 20 into a standard programming language, such as Java or C, or into a hardware description language, such as VHDL, and then applies a programming language compiler to prepare the new validated clinical rules 20 for deployment to, and integration into, the clinical rules module 16.

The development tool 46 may be configured to permit drafting and editing of the new clinical data and additional logic 26 prior to integration into the domain module 22. More particularly, the development tool 46 generally defines the new clinical data and additional logic 26 in a form readable and executable by the domain module 22 and prepares the new clinical data and additional logic 26 for deployment to, and integration into, the domain module 22.

The deployment tool 48 generally is configured to deploy from the development environment 12 to the deployed environment 14 the new validated clinical rules 20, the new clinical data and additional logic 26, and a configuration file 28. The new validated clinical rules 20 are deployed for integration into the clinical rules module 16, while the new clinical data and additional logic 26 are deployed for integration into the domain module 22. The configuration file 28 is deployed for directing the integration of the new validated clinical rules 20 and the new clinical data and additional logic 26. More particularly, once the new validated clinical rules 20, the new clinical data and additional logic 26 and, the configuration file 28 are received by the deployed application in the deployed environment 14, the configuration file 28 may be configured to instruct the deployed application to re-start. On start-up, the deployed application reads the configuration file 28, which may instruct the deployed application on which clinical rules 18, 20 to load in the clinical rules module 16 and which, if not both, clinical data and logic 24, 26 to load in the domain module 22. Thereafter, the loaded clinical rules, whether existing 18 or new 20, may be available for review by the individual and be used by the extensible system 10 to determine therapy by requesting information from either the exiting clinical data and base logic 24 or the new clinical data and additional logic 26, or both. As such, the configuration file 28 may be used to either replace existing clinical rules 18 or add new validated clinical rules 20 to the clinical rules module 16 without replacing the deployed application in the deployed environment.

Further, the deployment tool 48 may be configured to package the new validated clinical rules 20, the new clinical data and additional logic 26, and the configuration file 28 in a deployment package for simultaneous deployment to the deployed environment 14. This may ease the transmission of the new clinical rules 20, the new clinical data and additional logic 26, and the configuration file 28 over the network connection between the development environment 12 and the deployed environment 14 and may ensure substantially simultaneous reception by the clinical rules module 16 of the new validated clinical rules 20 and by the domain module 22 of the new clinical data and additional logic 26. It is contemplated that the deployment tool 48 also may be configured to deploy new messaging frameworks to the data request interface 30 and may incorporate the new messaging frameworks into a deployment package to the deployed environment 14.

The specific configuration of the deployment tool 48 may vary depending upon the specific deployed application utilized in the deployed environment 14. For example, but not bay way of limitation, if the deployed application is a Microsoft Windows® desktop system, then the deployment tool 48 may be configured as an install builder that may construct an install, which may include the deployment package and/or the individual components thereof, in the individual's deployed application for loading the new clinical rules 20 and the new clinical data and additional logic 26. As another example, if the deployed application is a J2ME (Java)-supported mobile device, such as, but not limited to, a personal data assistant or a cellular phone, then the deployment tool 48 may be configured as a JAR and/or JAD file builder to deploy such files to the mobile, wireless deployed application.

Figure 4:
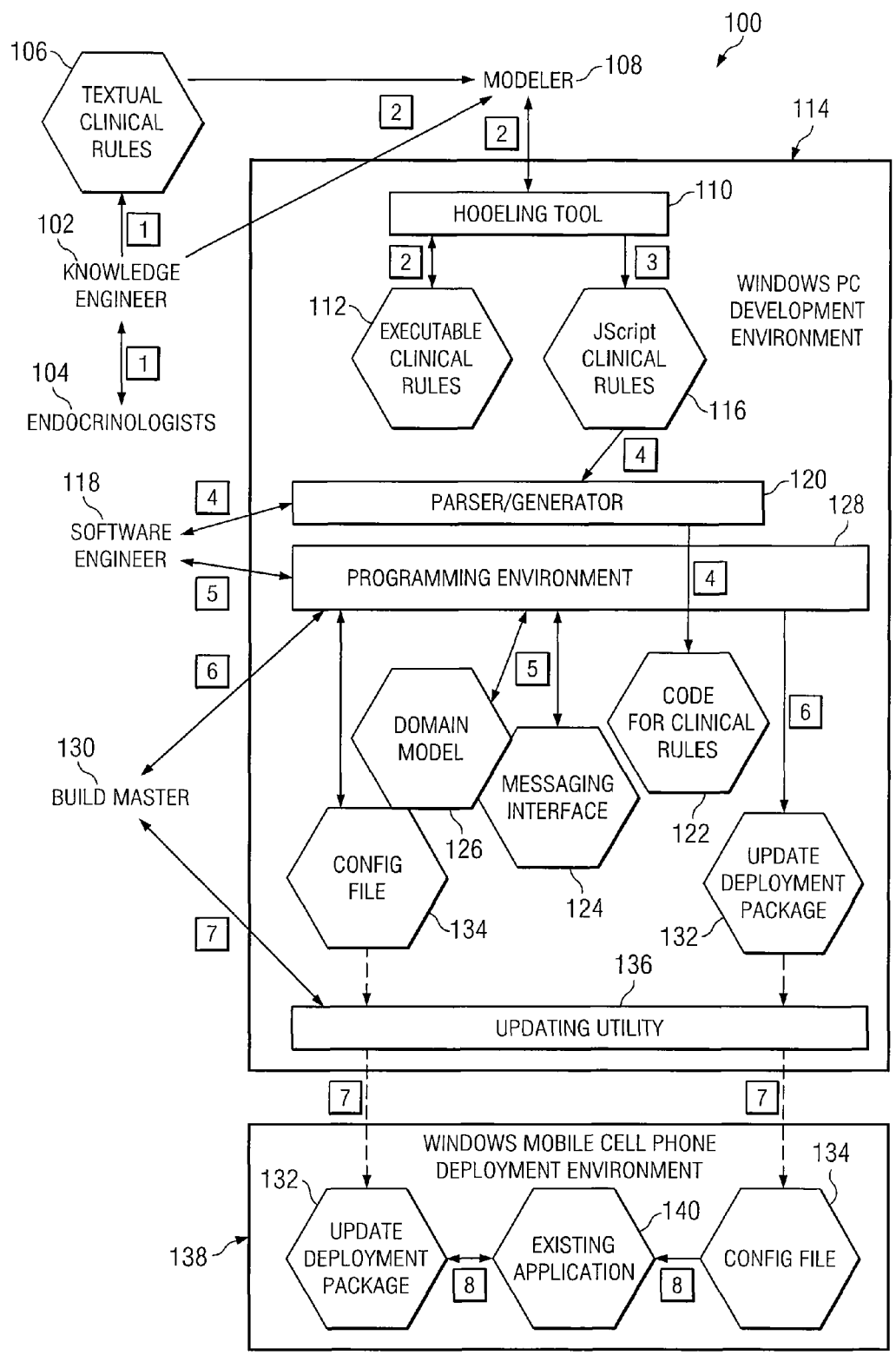
FIG. 4 is a diagram of an exemplary embodiment of a software development and deployment process to provide the new validated clinical rules, the new clinical data and additional logic, and the configuration file according to one embodiment of the present invention.

FIG. 4 is a diagram of an exemplary embodiment of a software development and deployment process 100 according to the present invention to provide the new validated clinical rules 20, the new clinical data and additional logic 26, and the configuration file 28. As shown in FIG. 4, this exemplary embodiment uses eight steps (the step number below correspond to the numbered boxes shown in FIG. 4):

1. A knowledge engineer 102 works with endocrinologists 104 to define textual clinical rules 106 for insulin dosing. These clinical rules 106 are captured in a text file on any computer system.
2. Next, the knowledge engineer 102 works with a modeler 108 to transform the clinical rules 106 using a software modeling tool 110 into a computer executable form 112. In one embodiment, the textual clinical rules 106 are transformed using the Vanguard Studio™ modeling tool on a computer 114, running such as for example, a Microsoft Windows™ operating system. In this form, the executable clinical rules 112 can be executed and debugged within the native computing environment, e.g., the Vanguard Studio environment. In other embodiment, other modeling tools which convert a text file into a form that may suitable read and executed by a computer running any other type of suitable operating system may be used.
3. Once the knowledge engineer 102 and modeler 108 are satisfied with the executable clinical rules 112, the modeler 108 uses the modeling tool 110 to produce a script file 116 that contains the rules, e.g., in Vanguard's Jscript language. In other embodiments, other scripting languages may be used.
4. A software engineer 118 then uses a parser/generator tool 120 that understands the language of the script file 116 to produce code 122 of the clinical rules in a suitable programming language. In one embodiment, the Jscript syntax of the script file 116 is read by the parser/generator 120 which produces a coded version of the rules in the C# programming language. In such an embodiment as depicted by FIG. 4, the programming code 122 for the clinical rules as generated in C# uses a messaging interface 124 (also defined in C#) to make requests against a domain model 126.
5. Using a programming environment 128, e.g. the Microsoft Visual Studio programming environment, on computer 114 or on a different computer, the software engineer 118 works with the newly generated programming code 126 for the clinical rules and the domain model 126 to verify that the domain model can properly respond to requests generated by the code 122 for the new clinical rules.
6. Once the software engineer 118 is satisfied with the code 122 for the new clinical rules and the domain model 126, a build master 130 uses the programming environment 128 (on the same computer 114 or a different computer) to produce deployment package 132 containing a compiled form of the code 122 for the new validated clinical rules, e.g., clinical rules 22, and the new clinical data and additional logic 26. In one embodiment, the deployment package 132 is provides as a new set of Microsoft .NET Compact Framework assemblies. The build master 130 also produces a configuration file 134 (e.g., configuration file 28) that tells the insulin advice application running on a device to load the new deployment package 132.

7. In one embodiment, the build master 130 uses an automated updating utility 136 such as, e.g., Microsoft's ActiveSync software, to transfer the new deployment package 132 and the configuration file 134 to a compatible device 138 such as, for example, a mobile cell phone, that has the insulin advice application 140 of the present invention (i.e., the existing clinical rules and the existing clinical data and base logic).

8. When the insulin advice application 140 on the device 138 is next started, it reads the configuration file 134 and loads and uses the new clinical rules and new clinical data and additional logic from the deployed package 132.

Referring again back to FIGS. 1-3, the extensible system 10 generally further comprises two or more input/output interfaces 32. At least one input/output interface generally is provided in the development environment 12 to assist in the drafting and editing of the new clinical rules 20 and the new clinical data and additional logic 26. In addition, at least one input/output interface 32 generally is provided with the deployed application in the deployed environment 14. The input/output interface 32 may be configured to exchange therapy-related data, clinical rule-related data, and/or other data with the individual, his/her physician, engineers, and/or others involved in utilizing the extensible system 10. Further, the input/output interface 32 may be configured to display data relating to physiological conditions of the individual, meals, recommended and delivered therapies, and/or any other therapy-related data.

The extensible system 10 may further comprise one or more metabolic sensors 34 in the deployed environment 14 that are configured to sense one or more metabolic parameters of the individual. These metabolic sensors 34 generally are operatively connected, wired or wirelessly, to the deployed application and, more particularly, are operatively connected to the domain module 22 such that data of the sensed metabolic parameters are transmitted from the metabolic sensors 34 and integrated into the existing clinical data and/or the new clinical data. In addition, the metabolic sensors 34 may be operatively coupled to the input/output interface 32 in the deployed environment 14, and, possibly, to an input/output interface 32 in the development environment 12 as well, such that the input/output interface 32 may display to the individual the metabolic parameters sensed by the metabolic sensors 34.

Also, the extensible system 10 generally comprises a therapy delivery device 36 in the deployed environment 14. The therapy delivery device 36 may be configured to deliver to the individual the therapy determined by the existing clinical rules 18 and the new validated clinical rules 20. The extensible system 10 may be configured such that the extensible system 10 requires the individual to approve therapy determined by the existing clinical rules 18 and the new validated clinical rules 20 prior to delivery of the determined therapy to the individual. Alternatively, the extensible system 10 may be configured such that the extensible system 10 delivers the therapy determined by the existing clinical rules 18 and the new validated clinical rules 20 to the individual without requiring approval of the determined therapy from the individual prior to delivery to the individual. Further, it is contemplated that embodiments of the extensible therapy delivery system 10 may comprise various other or additional components that may assist in the determination and/or delivery of therapy for an individual suffering from a chronic illness.

Figure 5:
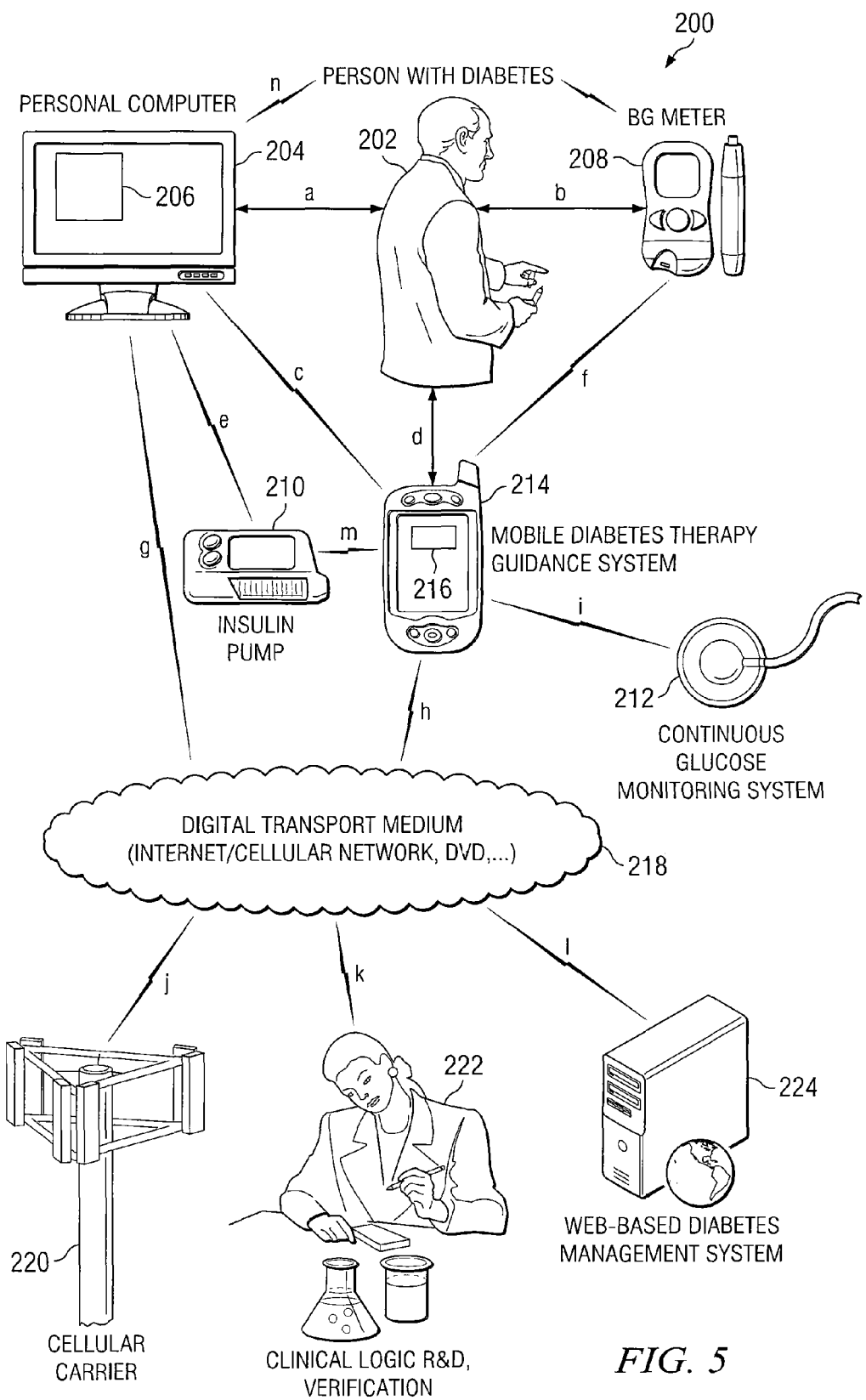
FIG. 5 is a diagram of an extensible therapy delivery system for determining therapy for a diabetic individual according to one embodiment of the present invention.

For example, FIG. 5 illustrates a few of such additional components that may be beneficial in a method 200 for managing treatment of diabetes or providing diabetes care. In the area of diabetes care, there are multiple possible applications of the invention that provide value to a person with diabetes (PWD) 202 and to a company 222 that produce software and hardware for diabetics (e.g., clinical logic research and development and verification). Typically, a person with diabetes (PWD) 202 will have multiple devices and software to help with the management of their disease. For example, it is assumed that the PWD 10 will have a personal computer 204 running software 206 for tracking health status which includes blood glucose (BG) measurements and insulin dosing, a blood glucose (BG) meter 208 for intermittent measurements, and optionally an insulin pump 210 for delivering insulin subcutaneously, a continuous glucose monitoring system 212 for monitoring blood glucose frequently, which may be subcutaneous and/or cutaneous, and/or a mobile diabetes therapy guidance system 214 running therapy guidance software 216, such as implemented on a mobile phone, a personal digital assistance, a notebook computer, and the like. As shown by FIG. 5 and in one embodiment, the PWD 202 interacts directly (arrows a, b, d) with the personal computer 204, the bG meter 208, and optionally, the therapy guidance system 214. For the purpose of this example and in another embodiment, the insulin pump 210 and the continuous monitoring system 212 is also used by the PWD 202 and configured through the software 206 of the personal computer 204, the therapy guidance software 216 of the therapy guidance system 214 or the BG meter 208. For this example and in other embodiments, devices 204, 208, 210, 212, and 214 contain operating software/firmware that embodies clinical logic to facilitate a PWD 202 to manage his or her diabetes care therapy. It is also to be appreciated that the device 204, 208, 210, 212, and 214 communicate (arrows e, c, f, and i) with each other in one form or another via wired or wireless data communications as is known.

In another embodiment of the invention, the therapy guidance system 214 contains clinical logic, for example, embodied in software for advising the PWD 202 on proper insulin dosing. In such an embodiment, when a new type of insulin with a new glucose-uptake profile is available to the PWD 202, changes to the clinical logic in the form of updates or a new version of the software provided on the therapy guidance system 214 may be needed. In such a circumstance, an R&D organization of the company 222 develops and will verify new clinical logic for dosing the new insulin type. Once the clinic logic is verified, the company 222 in one embodiment distributes the clinic logic electronically via an appropriate digital transport medium 218, such as a computer network (public and/or private, wireless and/or wired), a disc, portable memory devices, a web server, and the like.

In one embodiment, the digital transport medium 218 is a computer network facilitating a data transfer containing the new clinic logic from the company 222 (arrow k) to a partner cellular carrier providing a cellular network 220 (arrow j). In such an embodiment, the next time the PWD 202 activates the therapy guidance system 214, which in this embodiment is a cellular phone, and is communicating with the cellular network 220, the PWD 202 is given the option to install the new clinic logic on the therapy guidance system 214 (i.e., cellular phone). If the PWD 202 selects the option, the new clinical logic is downloaded (arrow h) to the cellular phone and the therapy guidance software 216 is upgraded. The PWD 202 will now have the option to employ the new insulin type with appropriate therapeutic guidance from the software 216.

In another embodiment, the company 222 of the insulin pump 210 develops a new approach for insulin delivery based on data from the continuous glucose monitoring system 212 which should only be applied to patients that meet a certain profile. In this embodiment, the company 222 develops and verifies the algorithm for the insulin pump 210 and the profile-testing logic for the desktop software 206. The company 222 in one embodiment uploads, via a data transfer (arrow k), the two updates to the digital transport medium 218, which in this embodiment is a web server. In one embodiment, when the user next starts the software 206 on the personal computer 204, the software 206 communicates (arrow g) with the web server (i.e., digital transport medium 218) and downloads the updates. The next time the insulin pump 210 communicates (arrow e) with the software 206 running on the personal computer 204, the software 206 queries the user whether to be evaluated for the new therapy; if the PWD 202 agrees, the software 206 executes the new profile-testing logic. If the PWD 202 meets the profile, the software 206 communicates (arrow e) with and updates the insulin pump 210 with the new insulin-delivery logic. The PWD 202 may then employ the configuration ability of the software 206 to choose the new therapy on the pump 210. In other embodiments, the insulin pump 210 communicates (arrow m) with the therapy guidance system 214 and the same updating and querying process is employed via software 216 which also communicates (arrow h) with the web server.

In another embodiment, the company 222 of the bG meter 208 and the monitoring system 212 have a refinement to a bG-calculation algorithm. In such a situation and in this embodiment, the company 222 after validating the refinement to the bG-calculation algorithm then transfers (arrow k) the refinement to the bG-calculation algorithm as an update on the web server (i.e. digital transport medium 218). When either software 206 or 216 communicates (arrows g or h, respectively) with the web server, the PWD 202 is informed that there is an update for the bG meter 208 and the monitoring system 212. The update is then downloaded to either or both devices 204 and 214, and the next time the software 206, 216 communicates (arrows i, f, and/or n) with the meter 208 and/or monitoring system 212, the software 206 or 216 will confirm with the PWD 202 to provide the update to the connected device 208 and/or 212. In one embodiment, once an update is received by the device 208 or 212, the device automatically incorporates the improved algorithm and immediately employs it in evaluating bG levels.

In still another embodiment, data to and from devices 204, 214 may be provided (arrows g, h) to a web-based diabetes management system 224 via (arrow l) the digital transport medium 218, such as provided in one embodiment as a public network (i.e., the Internet). Such a an embodiment is useful in providing updates to and from clinicians and medical health care providers with regards to the health condition of the PWD 202 and therapy actions and/or recommendations. It is to be appreciated that there other possible embodiments of this invention in the environment of FIG. 5, which is by no means exhaustive.

Figure 6:
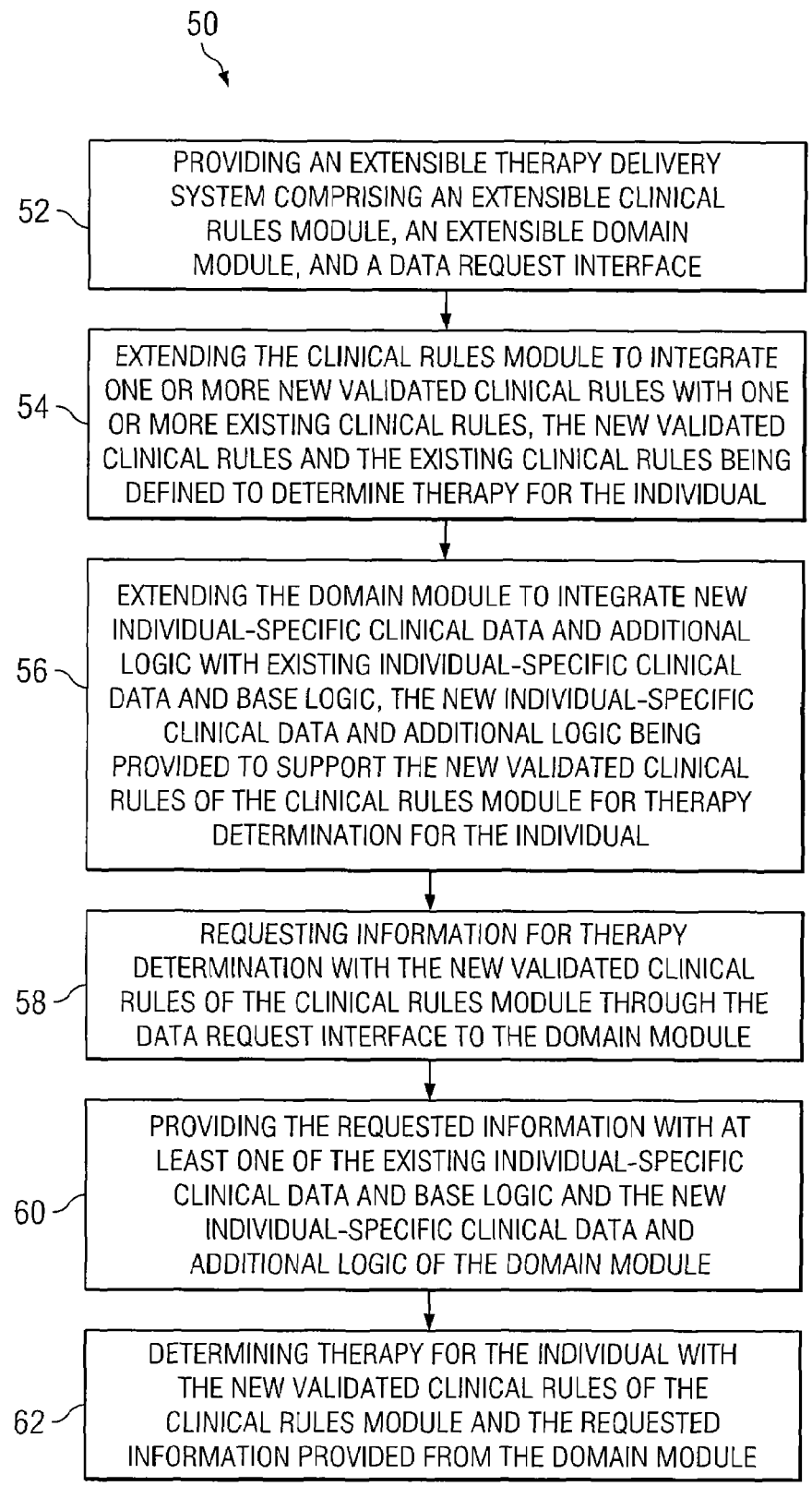
FIG. 6 is a process chart of a method of determining therapy for an individual with an extensible therapy delivery system according to one embodiment of the present invention.

Further, in accordance with another embodiment of the present invention, shown in FIG. 6, a method 50 of determining therapy for an individual with an embodiment of an extensible therapy system of the present invention is provided. More particularly, the method generally comprises an embodiment of an extensible therapy delivery system of the present invention being provided, the extensible system comprising an extensible clinical rules module, an extensible domain module, and a data request interface (block 52). The clinical rules module is extended to integrate one or more new validated clinical rules with one or more existing clinical rules, the new validated clinical rules and the existing clinical rules being defined to determine therapy for the individual (block 54). The domain module is extended to integrate new individual-specific clinical data and additional logic with existing individual-specific clinical data and base logic, the new individual-specific clinical data and additional logic being provided to support the new validated clinical rules of the clinical rules module for therapy determination for the individual (block 56). Thereafter, the new validated clinical rules of the clinical rules module request information for therapy determination through the data request interface to the domain module (block 58). The requested information is provided to the data request interface with at least one of the existing individual-specific clinical data and base logic and the new individual-specific clinical data and additional logic of the domain module (block 60). The therapy is then determined for the individual with the new validated clinical rules of the clinical rules module and the requested information provided from the domain module (block 62).

Figure 7:
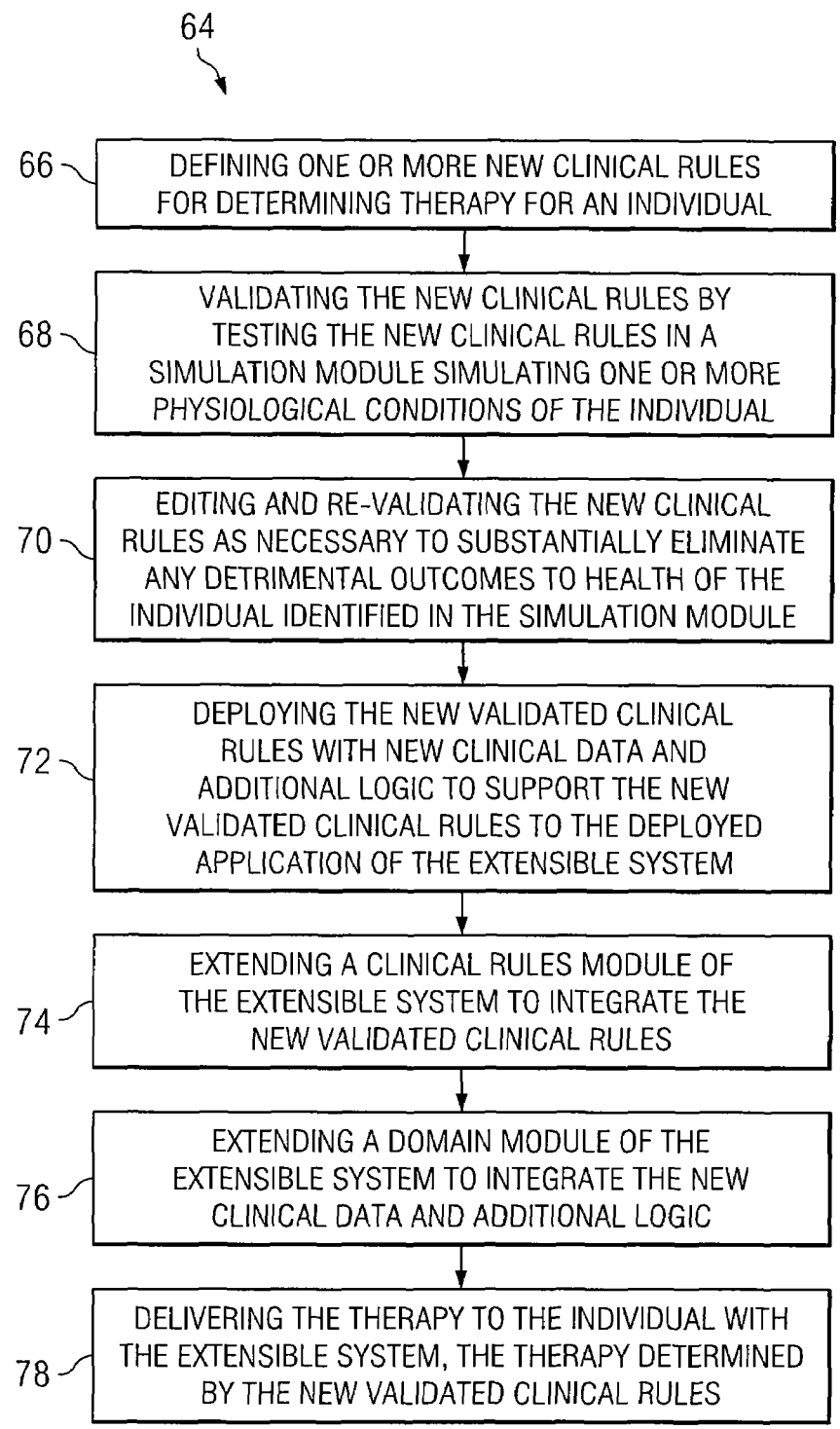
FIG. 7 is a process chart of a method of integrating new validated clinical rules in an extensible therapy delivery system according to one embodiment of the present invention.

In accordance with another embodiment of the present invention, shown in FIG. 7, a method 64 of integrating one or more new validated clinical rules in a deployed application of an embodiment of an extensible therapy delivery system of the present invention is provided. More particularly, the method comprises one or more new clinical rules being defined for determining a therapy for an individual (block 66). The new clinical rules are validated by testing the new clinical rules in a simulation module simulating one or more physiological conditions of the individual (block 68). The new clinical rules may be edited and re-validated as necessary to substantially eliminate any detrimental outcomes to health of the individual identified in the simulation module (block 70). Thereafter, the new validated clinical rules are deployed with new individual-specific clinical data and additional logic to support the new validated clinical rules for therapy determination to the deployed application of extensible system (block 72). A clinical rules module of the deployed application is extended to integrate the new validated clinical rules (block 74), while a domain module of the deployed application is extended to integrate the new individual-specific clinical data and additional logic (block 76). Therapy is then delivered to the individual with the deployed application of the extensible system, the therapy determined by the new validated clinical rules (block 78). It is contemplated that this method 64 may further comprise compiling the new validated clinical rules with new clinical data and additional logic to support the new validated clinical rules prior to their deployment to the deployed application of the extensible system.

It is noted that recitations herein of a component of the present invention being "configured" in a particular way or to embody a particular property, or function in a particular manner, are structural recitations as opposed to recitations of intended use. More specifically, the references herein to the manner in which a component is "configured" denotes an existing physical condition of the component and, as such, is to be taken as a definite recitation of the structural characteristics of the component.

It is noted that terms like "generally" and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present invention or to emphasize alternative or additional features that may or may not be utilized in a particular embodiment of the present invention.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

The foregoing description of the invention has been presented for purposes of illustration and description. It is not intended to be exhaustive or to limit the invention to the precise form disclosed, and other modifications and variations may be possible in light of the above teachings. The above embodiments disclosed were chosen and described to explain the principles of the invention and its practical application to thereby enable others skilled in the art to best utilize the invention. It is intended that the appended claims be construed to include other alternative embodiments of the invention except insofar as limited by the prior art. Therefore, having described the invention in detail and by reference to specific embodiments thereof, it will be apparent that modifications and variations are possible without departing from the scope of the invention defined in the appended claims.

What is claimed is:

1. An extensible therapy delivery system for an individual comprising:
    a development environment comprising a computer system having a simulation module;
    a deployed environment comprising an electronic device configured to be provided to the individual and integrated with a mobile deployed application which is operatively connected to the computer system in the development environment by a network connection, the mobile deployed application having:
        a clinical rules module comprising one or more existing clinical rules and which is configured to be extensible by receiving from the computer system of the development environment one or more new validated clinical rules;
        a domain module further comprising existing individual-specific clinical data and existing base logic, the domain module is configured to be extensible by receiving from the computer system of the development environment new individual-specific clinical data and additional logic to the existing base logic to support the one or more new validated clinical rules, wherein the one or more new validated rules are configured to be provided by the simulation module which is configured to simulate one or more physiological conditions of the individual and to validate the one or more new validated clinical rules via use of test data, wherein the simulation module is configured to validate the new clinical rules prior to integration into the clinical rules module by identifying detrimental health outcomes to the simulated physiological conditions of the individual caused by a simulated delivery of the therapy determined by the new clinical rules; and
        a messaging architecture having a data request interface operably connected to the clinical rules module and the domain module, wherein the messaging architecture comprises an existing messaging framework and is extensible to receive one or more new messaging frameworks to support requests for information made by the one or more new validated clinical rules to determine therapy for the individual, and wherein the clinical rules module is programmed to make a request for information to the data request interface according to the one or more existing clinical rules and the one or more new validated clinical rules in order to determine therapy for the individual, and the data request interface is programmed to forward the request to the domain module, which is programmed to answer the request using the new individual-specific clinical data and additional logic, if the existing individual-specific clinical data and the base logic are unable to answer the request, wherein the data request interface further comprises a failsafe module defining one or more therapy limitations independent of the one or more existing clinical rules and the one or more new validated clinical rules for substantially preventing delivery of determined therapy outside of the therapy limitations,
    and
    wherein the mobile deployed application is configured to deliver to the individual the therapy determined by the clinical rules module from using the answer to the request provided by the domain module, where the system comprises a clinical rule editing tool, a clinical rule compiler, a development tool, and a deployment tool employed in the development environment.

2. The extensible therapy delivery system according to claim 1, wherein the clinical rule editing tool is configured to permit drafting and editing of new clinical rules prior to integration into the clinical rules module.

3. The extensible therapy delivery system according to claim 1, wherein the clinical rule compiler is configured to convert the one or more new validated clinical rules into a form executable by the clinical rules module to determine therapy for the individual prior to integration into the clinical rules module.

4. The extensible therapy delivery system according to claim 1, wherein the development tool is configured to permit drafting and editing of the new individual-specific clinical data and additional logic prior to integration into the domain module.

5. The extensible therapy delivery system according to claim 1, wherein the deployment tool is configured to deploy from the development environment to the deployed environment via the network connection:
    the one or more new validated clinical rules for integration into the clinical rules module,
    the new individual-specific clinical data and additional logic for integration into the domain module, and
    a configuration file for directing the integration of the one or more new validated clinical rules and the new individual-specific clinical data and additional logic into the clinical rules module and the domain module, respectively.

6. The extensible therapy delivery system according to claim 1, wherein the therapy delivery system further comprises an input/output interface in the deployed environment, the input/output interface being configured to exchange therapy-related data with the individual.

7. The extensible therapy delivery system according to claim 6, wherein the input/output interface is configured to display data relating to physiological conditions of the individual, meals, and/or recommended and delivered therapies.

8. The extensible therapy delivery system according to claim 1, wherein the therapy delivery system further comprises one or more metabolic sensors in the deployed environment, the one or more metabolic sensors being configured to sense one or more metabolic parameters of the individual.

9. The extensible therapy delivery system according to claim 8, wherein the one or more metabolic sensors are operatively connected to the domain module such that data of the sensed metabolic parameters are transmitted from the one or more metabolic sensors and integrated into the existing individual-specific clinical data and/or the new individual-specific clinical data.

10. The extensible therapy delivery system according to claim 1, wherein the therapy delivery system further comprises a therapy delivery device in the deployed environment, the therapy delivery device being configured to deliver to the individual therapy determined by the one or more existing clinical rules and the one or more new validated clinical rules.

11. The extensible therapy delivery system according to claim 1, wherein the electronic device is a therapy delivery pump.

12. The extensible therapy delivery system according to claim 1, wherein extensibility of the clinical rules module and the domain module to receive the one or more new validated clinical rules and the new individual-specific clinical data and additional logic, respectively, do not interfere with an operational functionality of hardware or software of the system.

13. The extensible therapy delivery system according to claim 1, wherein therapy delivered to the individual by the system is insulin in a dosage amount, concentration, delivery rate, and/or delivery schedule determined by the one or more existing clinical rules and the one or more new validated clinical rules.

14. The extensible therapy delivery system according to claim 1 wherein the electronic device is selected from the group comprising a blood glucose meter, a mobile phone, a personal digital assistance, and a notebook computer.

15. A method of determining therapy for an individual, the method comprising:
providing an extensible therapy delivery system which comprises:
a development environment comprising a computer system having a simulation module, a deployed environment comprising an electronic device configured to be provided to the individual and integrated with a mobile deployed application which is operatively connected to the computer system in the development environment by a network connection, the mobile deployed application having:
a clinical rules module comprising one or more existing clinical rules and which is configured to be extensible by receiving from the computer system of the development environment one or more new validated clinical rules;
a domain module further comprising existing individual-specific clinical data and existing base logic, the domain module is configured to be extensible by receiving from the computer system of the development environment new individual-specific clinical data and additional logic to the existing base logic to support the one or more new validated clinical rules, wherein the one or more new validated rules are configured to be provided by the simulation module which is configured to simulate one or more physiological conditions of the individual and to validate the one or more new validated clinical rules via use of test data, wherein the simulation module is configured to validate the new clinical rules prior to integration into the clinical rules module by identifying detrimental health outcomes to the simulated physiological conditions of the individual caused by a simulated delivery of the therapy determined by the new clinical rules, and
a messaging architecture having a data request interface operably connected to the clinical rules module and the domain module, wherein the messaging architecture comprises an existing messaging framework and is extensible to receive one or more new messaging frameworks to support requests for information made by the one or more new validated clinical rules to determine therapy for the individual, and wherein the clinical rules module is programmed to make a request for information to the data request interface according to the one or more existing clinical rules and the one or more new validated clinical rules in order to determine therapy for the individual, and the data request interface is programmed to forward the request to the domain module, which is programmed to answer the request using the new individual-specific clinical data and additional logic, if the existing individual-specific clinical data and the base logic are unable to answer the request, wherein the data request interface further comprises a failsafe module defining one or more therapy limitations independent of the one or more existing clinical rules and the one or more new validated clinical rules for substantially preventing delivery of determined therapy outside of the therapy limitations, and wherein the mobile deployed application is configured to deliver to the individual the therapy determined by the clinical rules module from using the answer to the request provided by the domain module, where the system comprises a clinical rule editing tool, a clinical rule compiler, a development tool, and a deployment tool employed in the development environment;
extending the extensible clinical rules module to integrate one or more new validated clinical rules with one or more existing clinical rules, which result from testing one or more new clinical rules with test data in the simulation module simulating one or more physiological conditions of the individual, and the one or more new validated clinical rules and the one or more existing clinical rules being defined to determine therapy for the individual;
extending the extensible domain module to integrate new individual-specific clinical data and additional logic with existing individual-specific clinical data and base logic, the new individual-specific clinical data and additional logic being provided to support the one or more new validated clinical rules of the extensible clinical rules module for therapy determination for the individual;
requesting information for therapy determination with the one or more new validated clinical rules of the extensible clinical rules module through the data request interface to the extensible domain module;
providing the requested information to the data request interface with at least one of the existing individual-specific clinical data and the base logic, and the new individual-specific clinical data and additional logic of the extensible domain module; and determining therapy for the individual with the one or more new validated clinical rules provided from the simulation module and the requested information provided from the extensible domain module or defining one or more therapy limitations independent of the existing clinical rules and the new validated clinical rules from the failsafe module for substantially preventing delivery of therapy outside of the therapy limitations.

16. The method of determining therapy for an individual according to claim 15, further comprising on the computer system in the development environment:

defining one or more new clinical rules for determining a therapy for an individual or defining one or more therapy limitations for preventing delivery of therapy for the individual;

capturing the one or more new clinical rules in a text file on a computer;

validating the one or more new clinical rules by testing the one or more new clinical rules with test data in a simulation module simulating one or more physiological conditions of the individual;

editing and re-validating the one or more new clinical rules as necessary to substantially eliminate any detrimental outcomes to health of the individual identified in the simulation module;

deploying the one or more new validated clinical rules with new individual-specific clinical data and additional logic to support the one or more new validated clinical rules to the deployed application of the system;

extending a clinical rules module of the system to integrate the one or more new validated clinical rules;

extending an electronic device further comprising a domain module of the system to integrate the new individual-specific clinical data and additional logic; and delivering the therapy to the individual with the system, the therapy determined by the one or more new validated clinical rules or substantially preventing delivery of therapy to the individual determined by the one or more therapy limitations.

* * * * *

UNITED STATES PATENT AND TRADEMARK OFFICE
CERTIFICATE OF CORRECTION

PATENT NO.       : 8,589,178 B2
APPLICATION NO.  : 12/207975
DATED            : November 19, 2013
INVENTOR(S)      : Robert E. Reinke Page 1 of 2

It is certified that error appears in the above-identified patent and that said Letters Patent is hereby corrected as shown below:

In the Specification

Col. 4, Line 44, "safe module 31. The failsafe module 31 may defines one or"
should read --safe module 31. The failsafe module 31 may define one or--;

Col. 6, Line 22, "engineers may cooperate in using the clinical rule editing too"
should read --engineers may cooperate in using the clinical rule editing tool--;

Col. 7, Line 63, "bay way of limitation, if the deployed application is a"
should read --by way of limitation, if the deployed application is a--;

Col. 8, Line 13, "plary embodiment uses eight steps (the step number below"
should read --plary embodiment uses eight steps (the step numbers below--;

Col. 8, Lines 29-30, "ment, other modeling tools which convert a text file into a form that may suitable
read and executed by a com"
should read --ments, other modeling tools which convert a text file into a form that may be suitably
read and executed by a com--;

Col. 8, Line 66, "package 132 is provides as a new set of Microsoft .NET"
should read --package 132 is provided as a new set of Microsoft .NET--;

Col. 10, Line 16, "includes blood glucose (BG) measurements and insulin dos-"
should read --includes blood glucose (bG) measurements and insulin dos--;

Col. 10, Line 17, "ing, a blood glucose (BG) meter 208 for intermittent mea-"
should read --ing, a blood glucose (bG) meter 208 for intermittent mea- --;

Signed and Sealed this
Nineteenth Day of August, 2014

Michelle K. Lee
*Deputy Director of the United States Patent and Trademark Office*

CERTIFICATE OF CORRECTION (continued)
U.S. Pat. No. 8,589,178 B2

Col. 11, Line 53, "network (i.e., the Internet). Such a an embodiment is useful in" should read --network (i.e., the Internet). Such an embodiment is useful in--; and Col. 11, Line 57, "to be appreciated that there other possible embodiments of" should read --to be appreciated that there are other possible embodiments of--.